United States Patent [19]

Edlund et al.

[11] Patent Number: 5,217,506
[45] Date of Patent: Jun. 8, 1993

[54] HYDROGEN-PERMEABLE COMPOSITE METAL MEMBRANE AND USES THEREOF

[75] Inventors: David J. Edlund; Dwayne T. Friesen, both of Bend, Oreg.

[73] Assignee: Bend Research, Inc., Bend, Oreg.

[21] Appl. No.: 883,697

[22] Filed: May 15, 1992

Related U.S. Application Data

[63] Continuation-in-part of Ser. No. 734,177, Jul. 22, 1991, Pat. No. 5,139,541, which is a continuation-in-part of Ser. No. 566,092, Aug. 10, 1990.

[51] Int. Cl.$^5$ .................. B01D 53/22; B01D 71/02
[52] U.S. Cl. ............................. 55/16; 55/73; 55/158; 55/524
[58] Field of Search ............. 55/16, 68, 73, 158, 55/524; 427/125, 126.3, 405, 419.2, 419.7; 428/609, 629, 636, 661, 662

[56] References Cited

U.S. PATENT DOCUMENTS

| | | | |
|---|---|---|---|
| 3,350,846 | 11/1967 | Makrides et al. | 55/16 |
| 4,468,235 | 8/1984 | Hill | 55/16 |
| 4,496,373 | 1/1985 | Behr et al. | 55/16 |
| 5,139,541 | 8/1992 | Edlund | 55/16 |

*Primary Examiner*—Robert Spitzer
*Attorney, Agent, or Firm*—Chernoff, Vilhauer, McClung & Stenzel

[57] ABSTRACT

Various hydrogen production and hydrogen sulfide decomposition processes are disclosed that utilize composite metal membranes that contain an intermetallic diffusion barrier separating a hydrogen-permeable base metal and a hydrogen-permeable coating metal. The barrier is a thermally stable inorganic proton conductor.

15 Claims, 11 Drawing Sheets

5,217,506

HYDROGEN-PERMEABLE COMPOSITE METAL MEMBRANE AND USES THEREOF

The government has rights in this invention pursuant to Contract Nos. DE-FG03-91ER81228 and DE-FG03-91ER81229 awarded by the Department of Energy.

This is a continuation-in-part of application Ser. No. 07/734,177, filed Jul. 22, 1991 now U.S. Pat. No. 5,139,541, which is a continuation-in-part of application Ser. No. 07/566,092, filed Aug. 10, 1990.

BACKGROUND OF THE INVENTION

Metal membranes that are selectively permeable to hydrogen are known. See, for example, U.S. Pat. Nos. 4,388,479 and 3,393,098, both of which disclose Group V and VIII alloy membranes such as palladium alloy catalytic membranes. The prohibitively high cost of palladium has lead to efforts to fabricate composite hydrogen-permeable metal membranes by coating certain transition metal alloy base metals with palladium or palladium alloys. See, for example, U.S. Pat. Nos. 4,468,235 and 3,350,846. The coating on such base metals imparts chemical resistance to the base metal and in some cases increases the rate of adsorption of hydrogen onto the metal membrane surface. However, such coated metal membranes have an inherent shortcoming in that, under the elevated temperature conditions of use or fabrication by diffusion welding, the coating metal tends to diffuse into the base metal, thereby destroying the benefits available from such composite metal membranes. U.S. Pat. No. 4,496,373 discloses a nonporous hydrogen-permeable composite metal membrane that addresses this intermetallic diffusion problem for a base metal alloy of a specific composition coated with a palladium alloy of specific composition. However, the composition of the palladium alloy coating and the base metal alloy are narrowly defined so as to favor partitioning of the palladium into the coating alloy as opposed to the base metal alloy. Consequently, this approach is not general in nature, requires strict control over alloy composition, and allows for little variation in selection of metals for membrane fabrication.

These and other shortcomings of prior art hydrogen-permeable composite metal membranes are overcome by the present invention, which is summarized and described in detail below.

SUMMARY OF THE INVENTION

The present invention provides a novel nonporous composite hydrogen-permeable metal membrane and methods of using the same for the selective separation of hydrogen.

DETAILED DESCRIPTION OF THE INVENTION

The base metal of the metal membrane of the present invention is selected from hydrogen-permeable transition metals from Groups IIIB, IVB, VB, VIIB and VIIIB of the periodic table and alloys containing $\geq 20$ wt% of said metals, and may be from 25 to 250 microns in thickness.

The coating metal is a hydrogen-permeable transition metal that is chemically and physically stable at temperatures of at least 500° C., is preferably selected from the transition metals of Groups VIIB and VIIIB of the periodic table, most preferably Fe, Mn, Ni, Pd, Pt, Ru and alloys containing $\geq 20$ wt% of said metals, and preferably from 0.01 to 1.0 micron in thickness.

The intermetallic diffusion barrier is a thermally stable inorganic proton conductor other than pure metal or a pure metal alloy. "Proton conductor" refers not only to H+ion-conducting materials, but broadly to any material that shows complex ion motion at high temperatures, such as do the oxides and sulfides of molybdenum, silicon, tungsten and vanadium; doped $SrCeO_3$ ($SrCe_{1-x}M_xO_{3-\alpha}$ where x is from 0.05 to 0.10, $\alpha$ is a variable determined by the oxidation state of M, and M is a metal selected from Dy, In, Mg, Nd, Sm, Y, Yb, and Zn; see Iwahara et al., "Solid State Ionics", pp. 359–363 (1981)); $Zr(HPO_4)_2$; the glasses $PbO-SiO_2$, $BaO-SiO_2$, and $CaO-SiO_2$; the $M_3H(TO_4)_2$ family of crystals (where M is $NH_4^+$, K, Rb or Cs and T is S or Se); yttrium-substituted oxyhydroxyapatite; $\beta-Ca(PO_3)_2$; and $RbHSeC_4$.

In a most preferred form, the barrier is selected from the group consisting essentially of oxides of molybdenum, silicon, tungsten and vanadium, and sulfides of molybdenum, tungsten and vanadium, and is from 0.1 to 25 microns in thickness.

When the membrane of the present invention is used in the presence of hydrogen sulfide, the coating metal must be substantially resistant to chemical attack by that gas.

Figure 1:
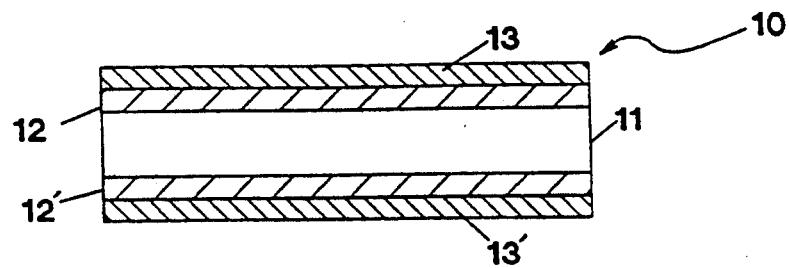
FIG. 1 is a schematic cross-sectional view of an exemplary composite membrane of the present invention.

Referring to FIG. 1, there is shown a preferred exemplary embodiment of a composite metal membrane 10 comprising a base metal layer 11, two intermetallic diffusion barrier layers 12 and 12' and two coating layers 13 and 13'. Although two layers 12 and 12' and 13 and 13' are shown, composite metal membranes having only single layers 12 and 13 also comprise useful embodiments of the present invention.

Figure 2:
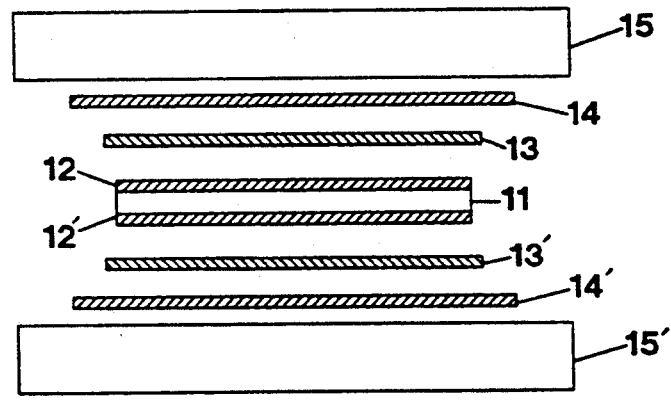
FIG. 2 is a schematic cross-sectional exploded view of an exemplary method of making the composite membrane of the present invention.

Fabrication of the composite metal membranes of the present invention is preferably by a temperature/pressure lamination of the three components. FIG. 2 schematically illustrates such a fabrication technique. In FIG. 2, there is shown an exploded cross-sectional view of the composite metal membrane of FIG. 1 prior to lamination, and wherein like numerals correspond to the same elements. In FIG. 2 there are shown graphite gaskets 14 and 14' and stainless steel press plates 15 and 15'. The graphite gaskets 14 and 14' seal the membrane against exposure to air during the lamination in order to protect against oxidation. The intermetallic diffusion barrier is preferably first applied chemically to the base metal by deposition thereon of an inorganic oxide or sulfide layer. In the case of oxides, the base metal may be coated by spraying, spinning or dipping with a solution of a precursor to the oxide, such as $SiCl_4$ (or $Si(OMe)_4$ with a catalytic amount of concentrated HCl), $WCl_6$ or $MoCl_5$, which then hydrolyzes to form the oxide layer. In the case of metal sulfide layers, the base metal may be simply exposed to a sulfide gas, such as hydrogen sulfide, at elevated pressure and temperature for a short time, such as 5 to 15 minutes. Alternatively, the base metal may be coated by spraying, spinning, or dipping with a solution of a precursor to the sulfide, such as $WCl_6$, $MoCl_5$ or $VCl_3$, which may then be reacted with hydrogen sulfide to form the sulfide layer. Yet another method for applying the oxide or sulfide layer is by vapor deposition of the desired oxide or sulfide onto the base metal.

The composite membrane of the present invention is selectively permeable to hydrogen gas and may be used in virtually any reaction where hydrogen is either a reactant or a product and is advantageously isolated, reflected in the two reaction schemes

A prime example of such a class of reactions is the separation of hydrogen from the petroleum-derived and coal-derived gases nitrogen, carbon monoxide, carbon dioxide, hydrogen sulfide, and water vapor in the form of steam. Another example of the above broad class of reactions is the decomposition of hydrogen sulfide in either bulk treatment or trace removal applications. Such applications include the simultaneous separation and decomposition of hydrogen sulfide from coal-derived gas, from sour natural gas, from refinery process streams, and from tail gases from Claus plants. Yet another example is in the production of olefins and aromatics by the thermal or catalytic dehydrogenation of a hydrocarbon feed to produce hydrogen.

Figure 3:
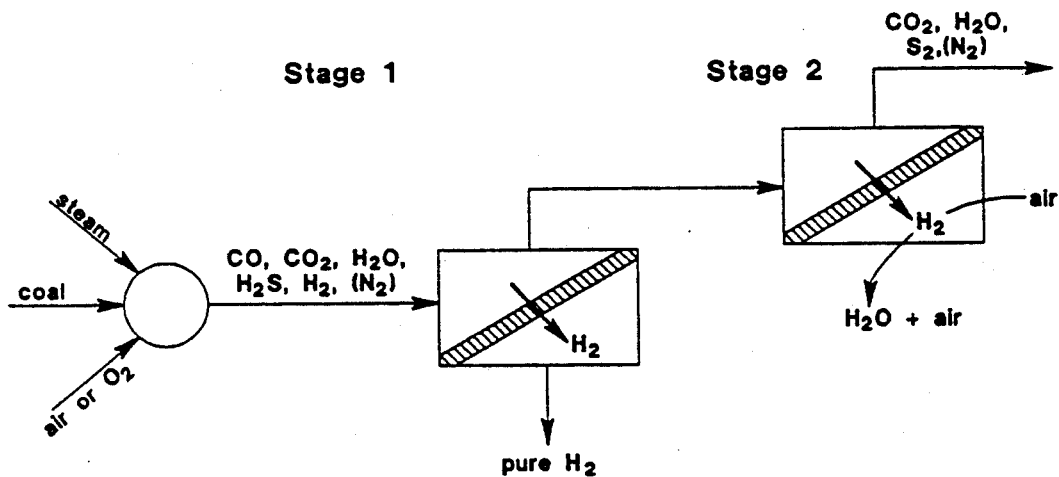
FIG. 3 is a schematic of an exemplary two-stage process for the production of hydrogen gas from coal-derived gases using the composite membrane of the present invention.

Referring to FIG. 3, there is depicted a two-stage membrane reactor process using the composite membrane of the invention to produce hydrogen from coal-derived gas. An especially preferred form of the composite membrane comprises an intermetallic diffusion barrier of the type described herein "sandwiched" between two layers comprising a base-metal layer and coating-metal layer consisting of platinum or a platinum-coated metal wherein the platinum metal is from 0.01 to 10 micron in thickness.

In the gasifier reactor preceding the Stage 1 reactor, coal, steam and air or oxygen are brought together to form CO, $CO_2$, $H_2O$, $H_2$, $H_2S$ and $N_2$ (if air is the oxygen source), which together form the feed to the Stage 1 reactor. In the Stage 1 reactor, which utilizes the composite membrane of the invention, hydrogen present in the feed selectively permeates the composite membrane. In addition, $H_2S$ present in the feed from the gasifier thermally decomposes to sulfur and hydrogen, and the latter also selectively permeates the composite membrane. Finally, the Water Gas Shift (WGS) reaction

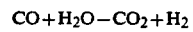

takes place in the Stage 1 reactor and the hydrogen produced also selectively permeates the composite membrane. The preferred conditions for the Stage 1 reactor are: temperature of at least 700° C. but less than 1500° C.; feed gas pressure of at least 100 psia but less than 1000 psia; permeate side partial pressure of hydrogen less than the partial pressure of hydrogen in the feed; and the ratio of partial pressures of water in the feed to carbon monoxide in the feed of at least 2, and preferably 3. Under these conditions, hydrogen makes up approximately 25-40% of the gases on the feed side of the composite membrane in the Stage 1 reactor, which results in a substantial partial pressure of hydrogen in the feed gas stream. This in turn is sufficient to alone constitute a driving force for the permeation of substantially pure hydrogen through the Stage 1 composite membrane, which may be recovered.

A WGS catalyst may be incorporated into the Stage 1 reactor at the feed side of the membrane to increase the overall rate of the WGS reaction. The required area of membrane is estimated for a given feed stream composition and operating temperature by relating hydrogen flux to the operating temperature and hydrogen partial pressure according to well-known physical relationships (see, for example, U.S. Pat. No. 4,468,235).

Figure 9:
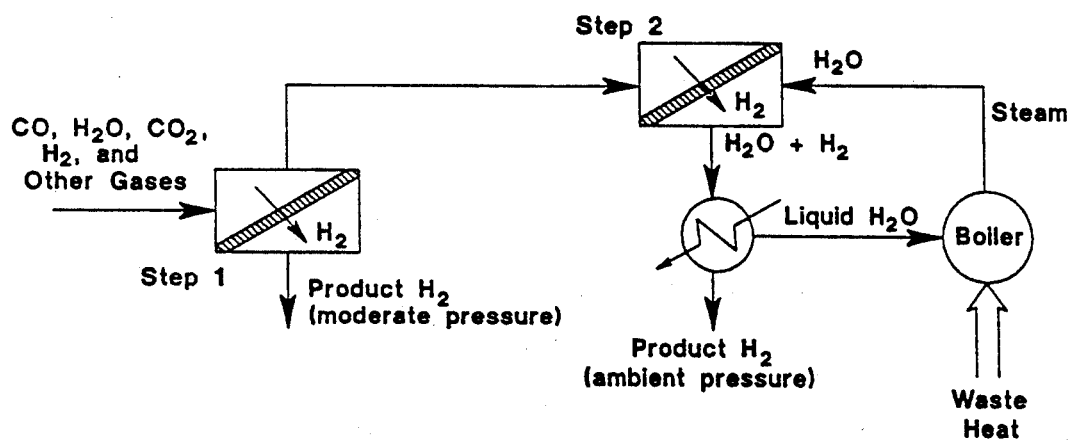
FIG. 9 is a schematic of an exemplary two-stage process using the composite membrane of the present invention to achieve high-equilibrium conversions and hydrogen product at moderate pressures.

As is shown in FIG. 9, Stage 1 in a process for the production of hydrogen from a feed gas derived from the WGS reaction may involve two separate steps to allow the recovery of the majority of the hydrogen at a moderately high pressure (20 psi to 60 psi) while recovering the balance of the hydrogen at ambient pressure in the second step that incorporates a condensable gas, such as steam, as a sweep gas. In this case, the yield of hydrogen remains very high (>98%) without sacrificing the pressure of the permeate hydrogen. For example, hydrogen might be removed from Step 1 at moderate pressure (say 50 psia), allowing the conversation to proceed to 90% to 95%. In Step 2, the conversion could be driven further (perhaps to 98% or 99%), and the permeate hydrogen recovered at ambient pressure by using steam as the sweep gas across the permeate side of the membrane.

In the Stage 2 reactor depicted in FIG. 3, the partial pressure of hydrogen resulting from the decomposition of $H_2S$ is relatively much lower than that for the Stage 1 reactor, and so an air sweep stream is used to provide the driving force for the permeation of hydrogen through the composite membrane, which oxidizes the remaining hydrogen to water. In an optional embodiment, steam may be used in place of the air sweep in Stage 2, combined with condensing and reusing the water vapor with an arrangement of the type described in connection with FIG. 8, which will lead to an overall hydrogen recovery of greater than 95%.

The process shown schematically in FIG. 3 and described above may also be applied to feed streams containing CO, $H_2O$, and $H_2S$ derived from the reforming of a hydrocarbon. If the hydrocarbon has first been desulfurized, Stage 2 of the process may be eliminated.

It is essential, in the case of sulfur-containing feed streams, for the metal membrane to remain permeable to hydrogen during exposure to $H_2S$ and for the metal membrane not to be corroded by $H_2S$. A key of this invention is the composition of a sulfur-resistant metal membrane and its use for producing pure hydrogen at useful pressures and in high yields, by driving the WGS reaction toward completion, from feed streams that contain sulfur, principally in the form of $H_2S$.

Industrial applications of the hydrogen recovery process depicted in FIG. 3 include use of the hydrogen as a fuel for fuel cells, as feedstock for the synthesis of synfuels and chemicals such as methanol and ammonia, and in petroleum refining.

Figure 4:
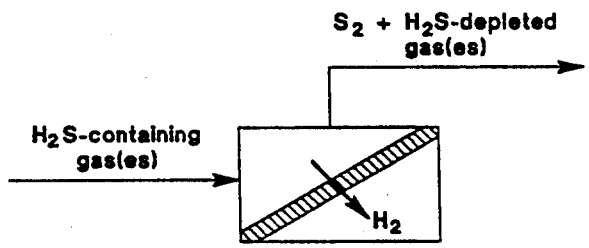
FIG. 4 is a schematic of a generic hydrogen sulfide decomposition process using the composite membrane of the present invention.

Referring to FIG. 4, there is depicted the basic scheme for use of the composite membrane of the invention in $H_2S$ decomposition processes, examples of which are depicted in FIGS. 5–8. $H_2S$-containing feed gas is fed to the feed side of the composite membrane in a reactor under conditions that cause the $H_2S$ to thermally decompose into sulfur and hydrogen, with the latter permeating the membrane. The raffinate comprises sulfur and $H_2S$-depleted gas(es). The same membrane preferred for the process depicted in FIG. 3 is preferred for the processes depicted in FIGS. 4–8. The preferred conditions for the $H_2S$ decomposition reactions are: temperature of at least 700° C., but less than 1500° C.; feed gas pressure of at least $10^{-4}$ psia but less than 1000 psia; permeate side partial pressure of hydrogen less than the partial pressure of hydrogen in the feed.

Industrial applications of the $H_2S$ decomposition processes depicted in FIGS. 4–8 include removal and decomposition of $H_2S$ from sour natural gas, from coal-derived gas, from refinery streams such as off gas from the hydrodesulfurization (HDS) of crude oil, and from Claus plant tail gas. Since high pressure does little to increase the partial pressure of hydrogen in the feed gas, the expense of a high pressure feed may be avoided.

Figure 5:
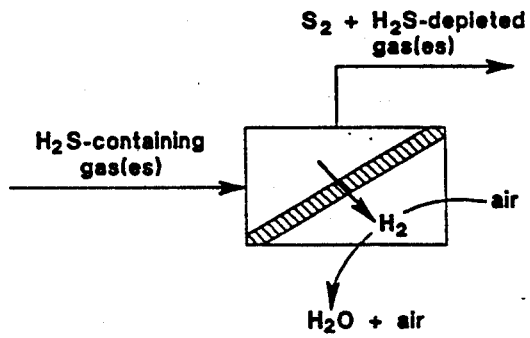
FIG. 5 is a schematic of an exemplary process for removal of trace amounts of hydrogen sulfide with the composite membrane of the present invention.

Referring to FIG. 5, there is depicted a $H_2S$ decomposition process that is ideally suited for removal of trace amounts of $H_2S$. Air is simply used as a sweep stream on the permeate side of the composite membrane of the invention to oxidize the resulting small amount of hydrogen permeating the membrane, converting the same to water, which may be disposed of.

Figure 6:
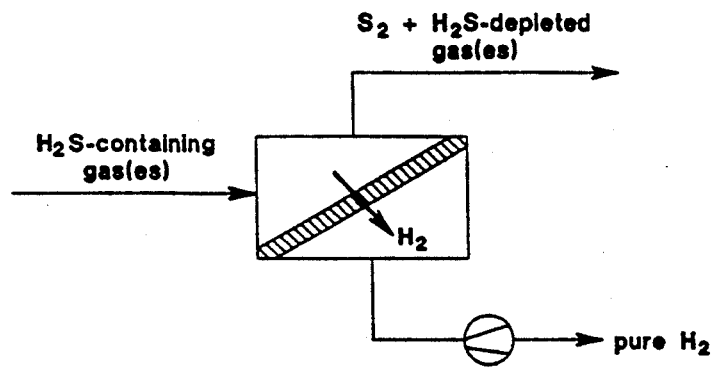
FIG. 6 is a schematic of an exemplary process for bulk treatment of hydrogen sulfide-containing gas(es) to obtain hydrogen gas using a vacuum pump and the composite membrane of the present invention.

Referring to FIG. 6, there is depicted a $H_2S$ decomposition process suitable for bulk treatment of $H_2S$-containing gas(es), where it is desired to recover substantially pure hydrogen. In such a process, a reduced pressure on the permeate side of the composite membrane of the invention is maintained, as by a vacuum pump. Such reduced permeate side pressure leads to a partial pressure of hydrogen on the permeate side that is less than that on the feed side, which provides the driving force for the removal of substantially pure hydrogen.

Figure 7:
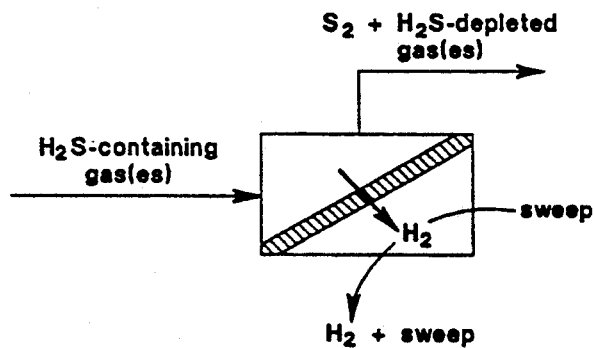
FIG. 7 is schematic of another exemplary process for bulk treatment of hydrogen sulfide-containing gas(es) to obtain hydrogen gas that uses a noncondensable sweep gas and the composite membrane of the present invention.

Referring to FIG. 7, there is depicted another $H_2S$ decomposition process suitable for bulk treatment of $H_2S$-containing gas(es), where it is desired to recover hydrogen diluted by a noncondensable sweep stream, such as Ar, $N_2$, $CO_2$, and He.

Figure 8:
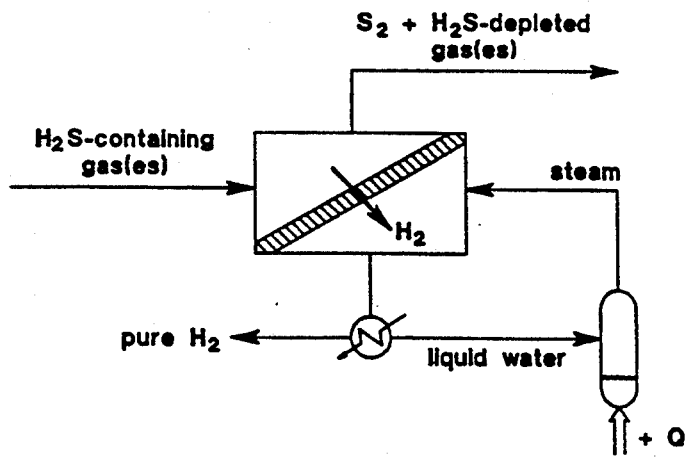
FIG. 8 is a schematic of still another exemplary process for bulk treatment of hydrogen sulfide-containing gas(es) to obtain hydrogen gas that uses a condensable sweep such as steam and the composite membrane of the present invention.

Referring to FIG. 8, there is depicted still another $H_2S$ decomposition process suitable for bulk treatment of $H_2S$-containing gas(es), where it is desired to recover substantially pure hydrogen, by use of a condensable sweep stream, such as steam. After permeated hydrogen is swept from the permeate side of the composite membrane of the invention, the condensable sweep component is condensed and recycled to a boiler for revaporization and reuse as a sweep, leaving substantially pure hydrogen as a recoverable off-gas from the condenser.

Figure 14:
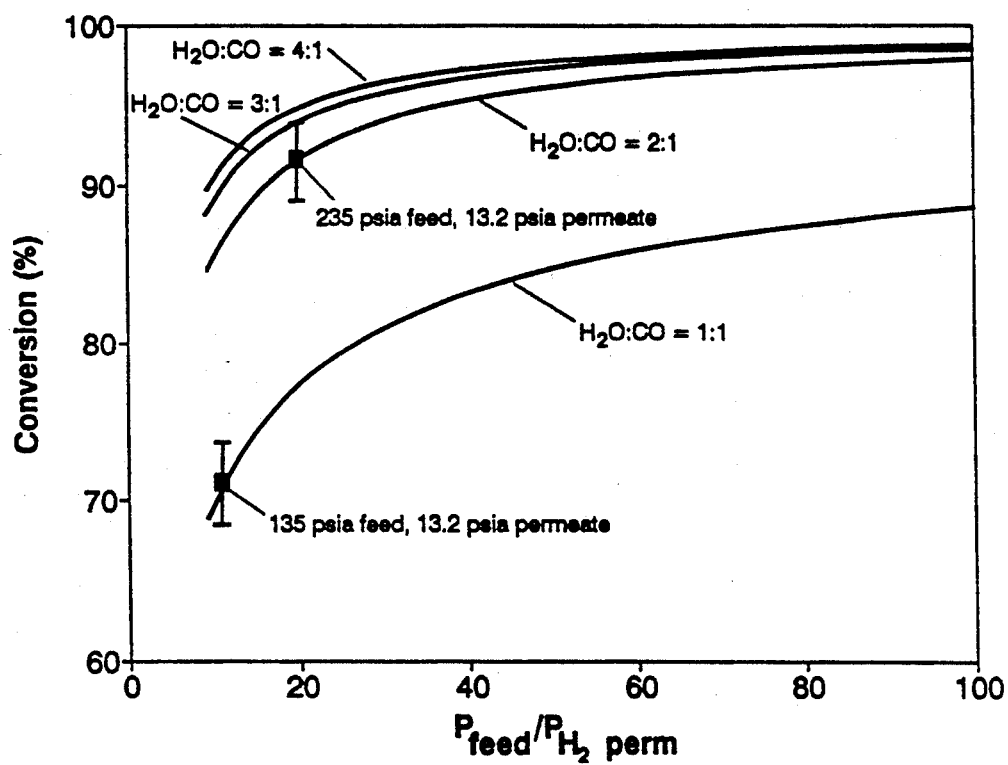

Because a primary objective of the membrane-based process (also known as a membrane reactor) is to produce pure hydrogen for subsequent use in downstream power generation and chemicals manufacture, the product hydrogen is more valuable, and the processing costs substantially less, if the hydrogen is delivered at as great a pressure as possible and reasonable. The key parameter, then, is the ratio of feed pressure to hydrogen permeate pressure, or $P_{feed}/P_{H2Perm}$. FIG. 14 shows the plot of calculated conversions against $P_{feed}/P_{H2perm}$ for several $H_2O/CO$ ratios.

Significantly, the experimentally measured equilibrium conversions in the membrane reactor at 700° C., using two $H_2O:CO$ ratios (1:1 and 2:1), are in close agreement with the calculated conversions, which are plotted in FIG. 14. Thus, it is reasonable to expect to achieve conversions of greater than 90% and approaching 100%, with sufficient residence time, by specifying the operating conditions from the calculated conversion plots in FIG. 14. These calculated plots assume a single-stage process for which residence times are sufficiently long to allow $P_{H2feed}$ to approach the permeate pressure. Taking the simple case of single-stage operation, these plots thus allow prediction of the highest conversions obtainable.

For example, at $H_2O:CO$ ratios typically used in coal gasification (about 4:1), conversions of at least 90% can be achieved at $P_{feed}/P_{H2perm} \geq 10$, while conversions of at least 95% can be realize at $P_{feed}/P_{H2perm} \geq 20$. In more meaningful terms, assuming the gasifier operates at 500 psia, then by holding the permeate hydrogen pressure at 50 psia, a maximum conversion of 90% can be achieved; a maximum conversion of 95% can be achieved at a permeate pressure of 25 psia. Pure hydrogen at these pressures is useful for powering fuel cells, although recompression would be needed if the hydrogen is to serve as a feedstock for chemicals or synfuels manufacture.

EXAMPLE 1

A $Ni/SiO_2/V$ composite metal membrane was made using the following procedure. A vanadium disc, 5 cm in diameter and 152 microns thick, served as the base metal, providing good mechanical properties to the composite membrane. Six-micron-thick nickel foil served as the coating material, providing chemical inertness to the composite membrane. A thin layer of $SiO_2$ between the vanadium and nickel prevented diffusion of the nickel coating into the vanadium base metal.

To fabricate the composite metal membrane, a thin layer of $SiO_2$ was deposited on both sides of the vanadium by dip-coating the vanadium disc with a 1M solution of $SiCl_4$ in methylene chloride at room temperature. As the methylene chloride solvent evaporated, the $SiCl_4$ rapidly hydrolyzed in the presence of atmospheric moisture to yield a film of $SiO_2$ approximately 25 microns thick. Good adhesion between the SiO$_2$ layer and the vanadium was observed. Next, the SiO$_2$-coated vanadium was laminated with the nickel foil at 700° C. under 20,000 pounds of pressure for 4 hours as shown schematically in FIG. 2 to produce the composite membrane. The composite membrane so prepared was flexible, and showed no sign of delamination when bent.

Hydrogen flux through the composite membrane was measured at 700° C. using a hydrogen gas feed stream at 100 psig (690 kPa), the permeated hydrogen being at ambient pressure. For comparison, the hydrogen flux through a control membrane made by laminating the same thickness of nickel foil directly to the same thickness of vanadium without the use of an intervening SiO$_2$ layer was measured under identical conditions. The results are given in the table below after 30 hours and 50 hours of operation. For this composite membrane, the layer that has the greatest resistance to hydrogen permeation (i.e., the layer that has the lowest hydrogen permeability) is the thin nickel coating (the limiting hydrogen flux through a nickel membrane 5 cm in diameter and 25 microns thick is 0.9 m$^3$/m$^2$·hr). Since the observed rate of hydrogen permeation through the composite membrane cannot exceed the rate of permeation through each chemically distinct layer of the membrane, the nickel coating of the Ni/SiO$_2$/V membrane limits the overall hydrogen flux.

| Membrane | H$_2$ Flux* (30 hrs) | H$_2$ Flux* (50 hrs) |
| --- | --- | --- |
| Ni/SiO$_2$/V | 0.9 | 0.6 |
| Ni/V | 0.15 | 0.006 |

*Average m$^3$/m$^2$·hr

As this Example shows, the Ni/SiO$_2$/V composite metal membrane shows higher flux and longer lifetime than the Ni/V control membrane indicating that the SiO$_2$ metal diffusion barrier is effective at preventing diffusion of the Ni coating into the vanadium base metal. There is no such barrier in the Ni/V control membrane to prevent diffusion of Ni into the vanadium and subsequent deterioration of the Ni coating. When the protective Ni coating deteriorates sufficiently, the vanadium base metal is exposed to feedstream impurities (N$_2$, O$_2$, and possibly other gases) that react with the vanadium metal, resulting in a decrease in the hydrogen permeability of the vanadium, which is manifested as a decrease in hydrogen flux through the Ni/V control membrane.

EXAMPLE 2

A NiCu/SiO$_2$/V composite metal membrane was made as follows. A vanadium disc, 5 cm in diameter and 152 microns thick, served as the base metal. NiCu foil (20 wt% Ni, 80 wt% Cu) 31 microns thick (made by laminating a 6-micron Ni foil to a 25-micron Cu foil) served as the coating material, providing chemical inertness to the composite membrane. A thin layer of SiO$_2$ between the vanadium and the NiCu coating served as the intermetallic diffusion barrier. A 25-micron-thick layer of SiO$_2$ was deposited on both sides of the vanadium by spin coating the vanadium with a 1M solution of Si(OMe)$_4$ in methanol containing a catalytic amount of concentrated HCl. The SiO$_2$-coated vanadium was laminated with the NiCu foil in substantially the same manner as in Example 1 with substantially the same results.

Hydrogen flux through the so-fabricated composite membrane was measured in the same manner as in Example 1. For comparison, the hydrogen flux through a control membrane made by laminating the same thickness of NiCu foil directly to the same thickness of vanadium without the use of an intervening SiO$_2$ layer was measured under identical conditions. The results are given in the table below after 72 hours of operation.

| Membrane | H$_2$ Flux* |
| --- | --- |
| NiCu/SiO$_2$/V | 2.4 |
| NiCu/V | 0.06 |

*Average m$^3$/m$^2$·hr

As is apparent, the composite metal membrane showed higher flux and longer lifetime than both the NiCu/V control membrane of this Example and the Ni/V control membrane of Example 1.

EXAMPLE 3

A Ni/V-sulfide/V composite metal membrane was made as follows. A vanadium disc, 5 cm in diameter and 152 microns thick, served as the base metal, while a 6 micron-thick Ni foil served as the coating material. A thin layer of vanadium sulfide served as the intermetallic diffusion barrier, which was deposited on both sides of the vanadium by exposing the vanadium disc to 30 psig H$_2$S at 700° C. for 10 minutes. Good adhesion between the vanadium sulfide layer and the vanadium was observed. The vanadium sulfide-coated vanadium was then laminated with the Ni foil at 700° C. under 20,000 pounds of pressure for 4 hours.

The hydrogen flux through the composite membrane was measured in the same manner as in Example 1 and compared with the hydrogen flux through a control membrane made by laminating the same thickness of Ni foil directly to the same thickness of vanadium under identical conditions without the use of an intervening sulfide-vanadium layer. The results after 50 hours of operation are given in the table below. As is apparent, the composite membrane showed higher flux and longer lifetime than the Ni/V control membrane. The flux through the composite membrane of this Example was less than that of Example 1 due to the lower hydrogen permeability of the vanadium sulfide layer relative to the SiO$_2$ layer.

| Membrane | H$_2$ Flux* |
| --- | --- |
| Ni/V-sulfide/V | 0.046 |
| Ni/V | 0.004 |

*Average m$^3$/m$^2$·hr

EXAMPLE 4

A Pd/SiO$_2$/V composite metal membrane was made as follows. A vanadium disc, 5 cm in diameter and 30 microns thick, served as the base metal, while a 25-micron-thick palladium foil served as the coating material. A thin layer of SiO$_2$ served as the intermetallic diffusion barrier. The SiO$_2$ layer was deposited on one surface of each of two 5-cm-diameter pieces of Pd foil by first placing a thin film of methanol containing a catalytic amount of HCl on the surfaces of the Pd, then, before the methanol/HCl evaporated, adding Si(OMe)$_4$ dropwise until each of the Pd surfaces was entirely covered; this yielded a 25-micron-thick SiO$_2$ layer by hydrolysis of the Si(OMe)$_4$ due to reaction with atmospheric moisture. The two pieces of $SiO_2$-coated Pd foil were placed $SiO_2$ layer down on both sides of the vanadium disc. The entire assembly was then placed directly in a permeation test cell and laminated in situ during permeation testing at 700° C. using the gas feed-pressure of 100 psi (690 kPa) to achieve lamination. The average hydrogen flux through the composite membrane was measured for nearly six hours and stabilized after about two hours at 25.3 $m^3/m^2$·hr. This high flux is a result of using palladium as the coating metal, rather than nickel or nickel/copper alloy, which has a greater permeability to hydrogen than do nickel or nickel/copper alloys.

For comparison, the hydrogen flux through a control membrane made by laminating the same thickness of palladium foil directly to the same thickness of vanadium foil without the use of an intervening $SiO_2$ layer was measured under identical conditions. The flux through this control membrane decreased steadily from the initial value of 19 $m^3/m^2$·hr to 14 $m^3/m^2$·hr after 6 hours, then to 0.91 $m^3/m^2$·hr after 50 hours operation. As is apparent, the composite membrane exhibited higher flux and longer lifetime than the Pd/V control membrane.

EXAMPLE 5

To demonstrate high permeability of the $SiO_2$ layer, a Pd/$SiO_2$/Pd composite metal membrane was made. Palladium served as the coating metal and the base metal was omitted. Palladium foil, 5 cm in diameter and 25 microns thick, was coated on one side with a thin layer of $SiO_2$ as in Example 4. Another piece of palladium foil of the same dimensions was then placed over the $SiO_2$-coated palladium so that the $SiO_2$ layer was between the two. The assembly was then placed in a permeation test cell and laminated in situ as in Example 4. The average hydrogen flux through the composite membrane was measured and observed to stabilize at 31 $m^3/m^2$·hr.

EXAMPLE 6

To demonstrate the high permeability of a $WO_3$ layer for use as a metal-diffusion barrier, a Pd/$WO_3$/Pd composite metal membrane was made. Palladium served as the coating metal and the base metal was omitted. Palladium foil, 5 cm in diameter and 25 microns thick, was coated on one side with a thin layer of $WO_3$ by applying to one surface a solution of $WCl_6$ in a mixture comprising about 94% methylene chloride, about 5% acetonitrile, and about 1% $Si(OMe)_4$. The $WCl_6$ rapidly hydrolyzed in the presence of atmospheric moisture to yield a thin film of $WO_3$. Another piece of palladium foil of the same dimensions was then placed over the $WO_3$-coated palladium so that the $WO_3$ layer was between two layers of palladium. The assembly was then placed in a permeation test cell and laminated in situ as in Example 4. The average hydrogen flux through the composite membrane was measured and observed to stabilize at 42 $m^3/m^2$·hr.

EXAMPLE 7

To demonstrate the high permeability of a $MoO_3$ layer for use as a metal-diffusion barrier, a Pd/$MoO_3$/Pd composite metal membrane similar to that of Examples 5 and 6 was made as follows. Palladium foil, 5 cm in diameter and 25 microns thick, was coated on one side with a thin layer of $MoO_3$ by applying to one surface a solution of $MoCl_5$ in the same solvent mixture as in Example 6. The $MoCl_5$ rapidly hydrolyzed in the presence of atmospheric moisture to yield a thin film of $MoO_3$. Another piece of palladium foil of the same dimensions was then placed over the $MoO_3$-coated palladium so that the $MoO_3$ layer was between the two pieces of palladium. The assembly was then placed in a permeation test cell and laminated in situ as in Example 4. The average hydrogen flux through the composite membrane was measured and was observed to stabilize at 67 $m^3/m^2$·hr.

EXAMPLE 8

A Ni/$MoO_3$/Cu composite metal membrane was made as follows. A copper disc, 5 cm in diameter and 250 microns thick, served as the base metal, while a 25-micron-thick nickel foil served as the coating material. A thin layer of $MoO_3$ served as the metal diffusion barrier, and was deposited on one surface of each of two pieces of 5-cm-diameter nickel foil as in Example 7. The two pieces of $MoO_3$-coated nickel foil were placed $MoO_3$-side down on both sides of the copper foil. The entire assembly was then placed directly in a permeation test cell and laminated in situ during permeation testing as in Example 4. Average hydrogen flux through the composite membrane was measured and observed to stabilize at 0.37 $m^3/m^2$·hr. This flux is identical to that through a copper membrane (250 microns thick, 5 cm diameter) under the same conditions of temperature and hydrogen pressure. Therefore, as expected, the copper base-metal layer is the limiting factor in the overall flux through this composite membrane.

EXAMPLE 9

A Pt-Pd/$SiO_2$/V composite metal membrane was made in substantially the same manner as in Example 1 except that 25-micron-thick platinum foil was used instead of the nickel foil for the coating material on the feed side of the membrane, and 25-micron-thick palladium foil was used instead of the nickel foil for the coating material on the permeate side of the membrane. (Platinum is used on the feed side of the membrane to provide chemical resistance to $H_2S$ in the feed stream. Because the permeate stream does not contain $H_2S$, the less expensive and more permeable coating metal palladium is used on the permeate side of the membrane.) Hydrogen flux through this membrane was evaluated with respect to two variables: the thickness of the Pt coating layer, and the temperature.

Flux is inversely proportional to the thickness of the membrane layer that offers the dominant (greatest) resistance to permeation. In this case, Pt offers the greatest resistance to hydrogen permeation as is shown by the following experimental results. Membranes containing 25- and 50-micron thicknesses of the Pt coating layer on the feed side of the membrane were evaluated. The overall thickness of these membranes was 90 or 115 microns, depending on the Pt coating thickness. These evaluations were done at 700° C. and 100 psig hydrogen feed pressure, with the permeate at ambient pressure. The results are plotted in FIG. 10, where J denotes flux in units of $m^3/m^2$·hr at 100 psi and L is the thickness of the Pt coating in microns. The data support the predicted inverse relationship (passing through zero at infinite thickness) between flux and thickness of the Pt coating layer, indicating that Pt is the layer that offers the greatest resistance to hydrogen permeation. (If the reaction $H_2 \rightarrow 2H$ were rate limiting at some thickness, flux would reach an asymptotic limit.)

Figure 10:
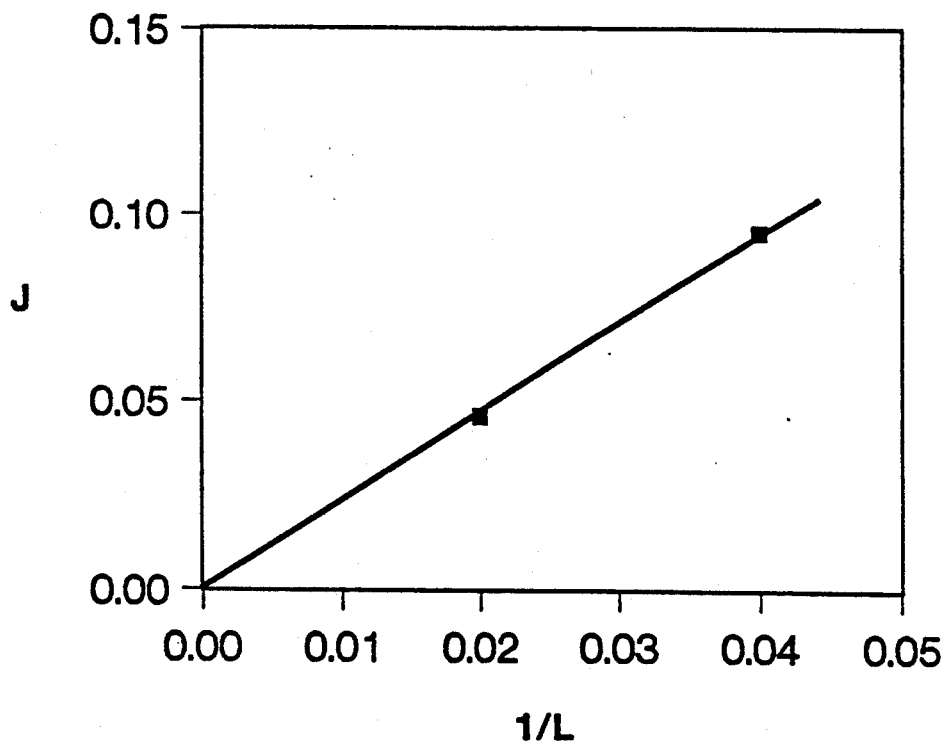
FIGS. 10–16 are graphs showing plots of various data obtained and predicted from processes using the composite membrane of the present invention.

Based on the experimental results shown in FIG. 10, the hydrogen flux for Pt thicknesses of 1 μm is estimated to be about 2.4 m³/m²·hr (8 SCFH/ft²) at 100 psig hydrogen. This estimated flux assumes that the other layers of the composite metal membrane (i.e., the SiO₂ layers, the vanadium layer, and the Pd layer are all much more permeable to hydrogen than is the Pt layer.

Flux was also shown to be dependent on temperature; it increased exponentially with increasing temperature. The flux was determined for both a composite metal membrane of Pt/V/Pd having a 25-μm-thick Pt coating on the feed side of the membrane and for a 25-μm-thick foil membrane at 600° C. and 700° C. (100 psig hydrogen feed pressure). The results are presented in FIG. 11 as a plot of influx in units of m³/m²·hr at 100 psi against reciprocal absolute temperature in degrees Kelvin (an Arrhenius plot) The data for both the composite metal membrane (dots) and the Pt foil (squares) fall on the same line because the Pt coating of the composite metal membrane is the major resistance to hydrogen permeation. Thus, the composite metal membrane, 90 μm thick in this case, exhibits flux characteristics as if it were simply a 25 μm-thick Pt foil.

Figure 11:
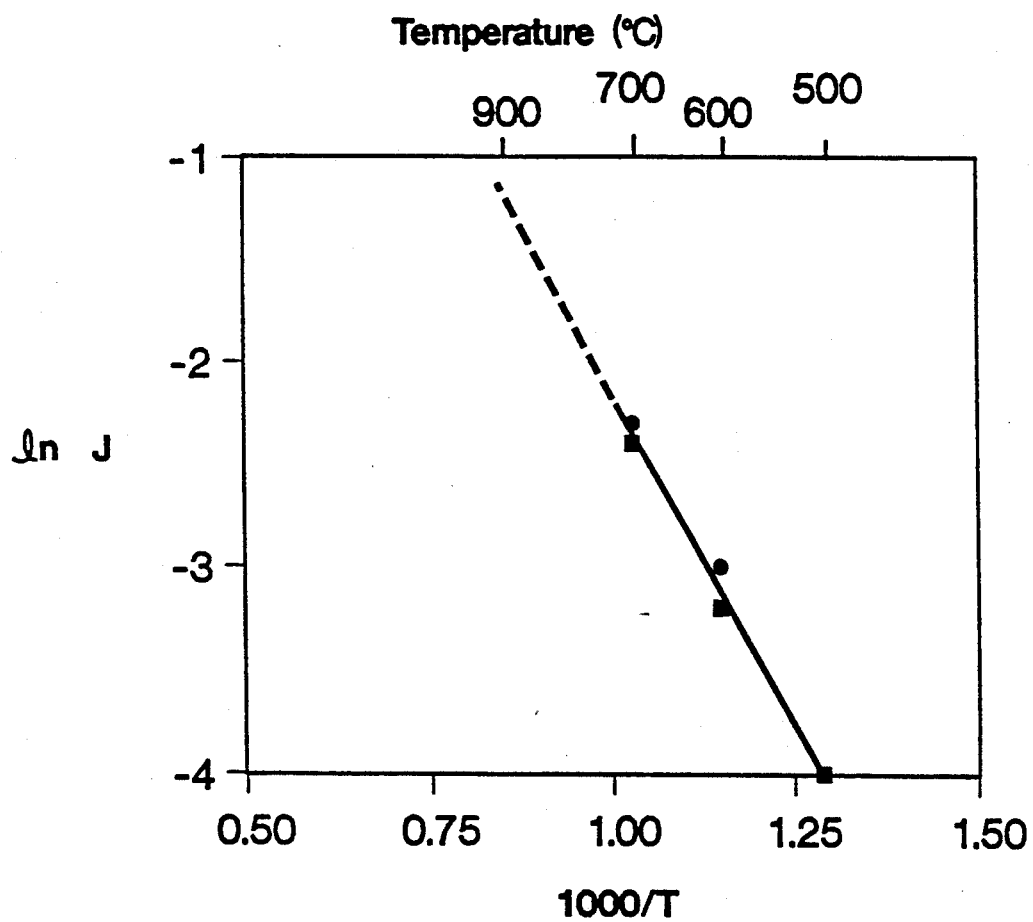

The Arrhenius plot of FIG. 11 allows the hydrogen flux to be estimated at potential operating temperatures greater than 700° C. Thus, if the operating temperature were raised to 800° C., the expected flux would be about 1.5 (±0.2) times greater than the observed flux at 700° C. For example, the combination of a reduction in the Pt thickness to 1 μm and operation of the membrane at 800° C. is expected to yield a flux of about 3.7 m³/m²·hr at 100 psig hydrogen. As before, this assumes that the Pt coating remains as the layer of least permeability to hydrogen when the temperature is increased to 800° C.

The temperature dependence of the hydrogen flux arises from the activation energy for diffusion of hydrogen atoms through the metal membrane. The activation energy, $E_a$, can be obtained from the slope of the Arrhenius plot, given as $$P_e = P_0 e^{-E_a/RT}, \text{ and}$$

$$P_e = \frac{JL}{(\sqrt{P_{H2feed}} - \sqrt{P_{H2perm}})}$$

where $P_e$ is the observed permeability of the membrane at the absolute temperature T (in degrees Kelvin), and $P_O$ is the pre-exponential permeation constant, R is the gas constant, and L is the thickness of membrane in microns, or membrane layer of greatest resistance to permeation. Thus, the slope of the Arrhenius plot corresponds to the value for $-E_a/R$ and the intercept corresponds to the value for $P_O$. For the Pt-coated composite metal membrane, the calculated values of $E_a$ and $P_O$ are listed in the table below. For comparison, the table also lists the literature values of $E_a$ and $P_O$ for Pt.

| Value | Pt-Coated Composite Metal Membrane | Pure Pt Metal |
|---|---|---|
| $E_a$(cal/mol) | 13,500 | 18,000 to 19,800 |
| $P_0 = \dfrac{cm^3(STP) \cdot mm}{cm^2 \cdot sec \cdot \sqrt{atm}}$ | 0.015 | 0.012 to 0.26 |

Experimentally determined values and the reported values for pure Pt are in reasonable agreement. Since the experiment yields values for $E_a$ and $P_O$ for the composite metal membrane (consisting of a Pt coating layer on the feed side of the membrane, SiO₂ layers, vanadium layer, and Pd layer on the permeate side of the membrane), the similarity between $E_a$ and $P_O$ for the composite membrane and for pure Pt indicates that Pt is the layer of greatest resistance to hydrogen permeation. If, for example, the permeability of the Pt layer were comparable to, or greater than, the permeability of the vanadium layer, it would be expected that observed values of $E_a$ and $P_O$ for the composite metal membrane would be closer to he values of $E_a$ and $P_O$ reported for vanadium--i.e., $E_a$ of about 3000 cal/mol and $P_O$ of about 0.2 cm³·mm/cm²·sec·√atm.

EXAMPLE 10

The WGS reaction will be driven toward completion if the reaction is conducted at the feed side of a Pt-Pd/SiO₂/V membrane such that hydrogen is removed from the feed side of the membrane. The rate at which hydrogen is removed from the feed side of the membrane is expected to increase exponentially with increasing temperature. This is because as the temperature increases, both the kinetics of the WGS reaction and the hydrogen flux will increase. At sufficiently long residence times, conversion will approach an equilibrium value defined by the temperate, the feed composition (H₂O:CO ratio), and the partial pressure of hydrogen remaining at the feed side of the membrane.

Figure 12:
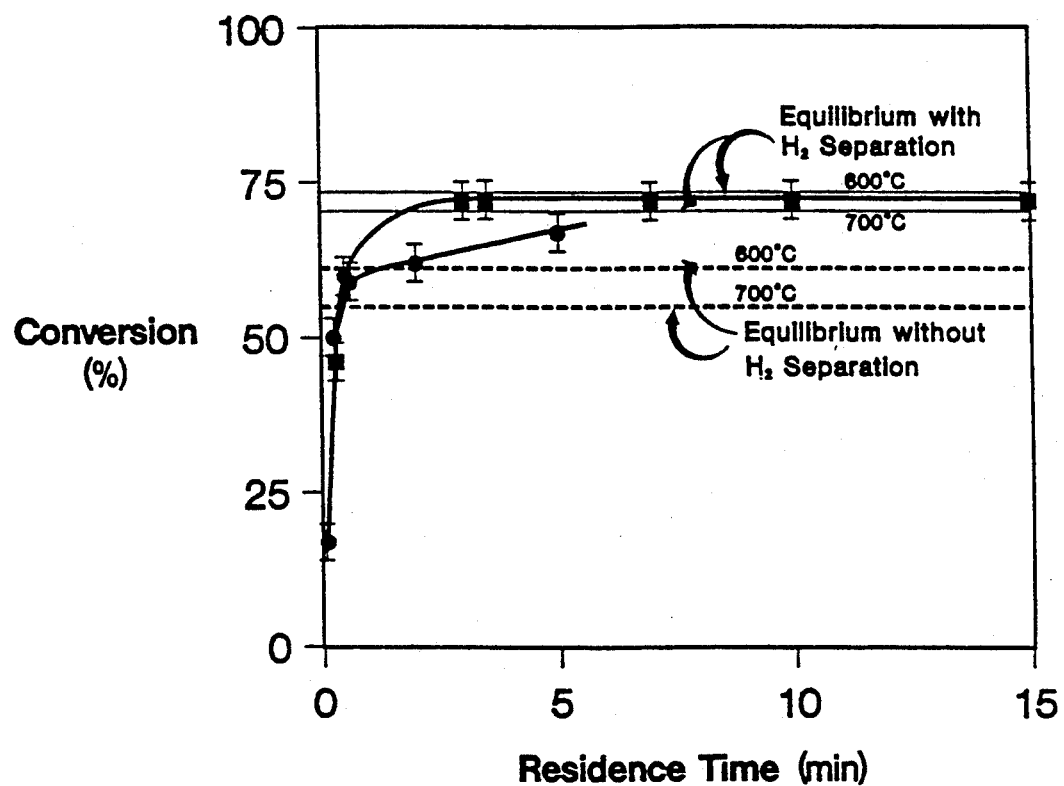

Using the Pt-Pd/SiO₂/V membrane described in Example 9, conversion was evaluated as a function of residence time at 600° C. (dots) and 700° C. (squares) for a feed stream at 135 psia with an H₂O:CO ratio of 1:1. The results are shown in FIG. 12. Equilibrium conversions, assuming hydrogen is not removed from the feed side of the membrane, at 600° C. (61%) and at 700° C. (55%), are shown by the dashed lines. The solid horizontal lines are the equilibrium conversions at 600° C. and at 700° C. with separation of hydrogen at the feed side of the membrane, and where the hydrogen concentration is reduced to ambient pressure, about 13.2 psia (equal to the permeate partial pressure of hydrogen). These equilibrium conversions were calculated from the WGS equilibrium constant, assuming that $P_{H2feed} = P_{H2perm}$.

FIG. 12 also shows the experimental data showing the approach to equilibrium for the 600° C. and 700° C. runs. For residence times greater than 2 minutes, the data was obtained from batch experiments, while flow experiments yielded data at the shorter residence times. At both temperatures, the WGS reaction was driven toward high conversion by the removal of hydrogen from the feed side of the membrane. At 700° C. the experimentally observed conversion reached the theoretically predicted limiting value of 71% ±3. This shows that the conversion can be driven beyond the normal equilibrium value by removal of hydrogen. As expected, the rate of approach to the limiting value was much faster at 700° C. than at 600° C.

EXAMPLE 11

Figure 13:
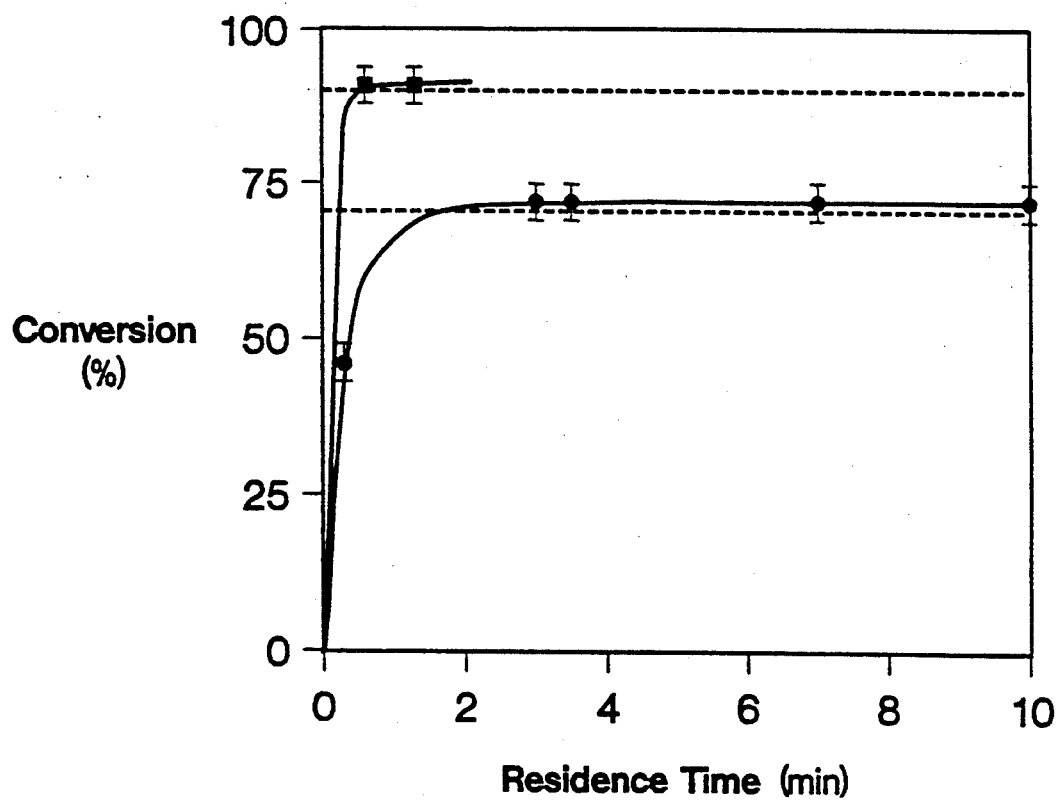

The WGS reaction, as conducted conventionally (without hydrogen removal), is not affected by changing pressure because there is no change in the number of moles of gas; i.e., one mole of H₂O and one mole of CO react to yield one mole of H₂ and one mole of CO₂. Increasing the feed pressure is expected to increase the conversion since a larger fraction of the product hydrogen can be removed concurrently with reaction. This was demonstrated experimentally, using the Pt-Pd/SiO$_2$/V membrane described in Example 9, by the data plots in FIG. 13, which show % conversion against residence time at 700° C. at feed pressures of 135 psia (dots) and 235 psia (squares).

Conversion in excess of 90% was achieved at the higher feed pressure (upper dashed horizontal line); without hydrogen separation the equilibrium conversion would have been only 73% (lower dashed horizontal line). The H$_2$O:CO ratio in this experiment was 2:1. For the feeds at both 135 and 235 psia, the final or equilibrium conversion is in very good agreement with the calculated conversion, assuming that the hydrogen partial pressure at the feed side of the membrane was reduced to a value equal to the permeate pressure (13.2 psia).

The driving force for hydrogen permeation through membrane is expressed as ln-mean driving force =

$$\frac{(\sqrt{P_{H2feed}} - \sqrt{P_{H2perm}}) - (\sqrt{P_{H2raff}} - \sqrt{P_{H2perm}})}{\ln \frac{\sqrt{P_{H2feed}} - \sqrt{P_{H2perm}}}{\sqrt{P_{H2raff}} - \sqrt{P_{H2perm}}}}$$

where $P_{H2feed}$, $P_{H2perm}$ and $P_{H2raff}$ represent the partial pressure of hydrogen in the feed, permeate, and raffinate streams, respectively.

Equilibrium was reached faster in the case of the higher-pressure feed for two reasons. First, the driving force for hydrogen permeation is greater for the feed stream at 235 psia (25 psi) than for the feed stream at 135 psia (19.5 psi). Second, the WGS reaction rate also increases as the feed pressure increases.

EXAMPLE 12

The thermal decomposition of H$_2$S will be driven toward complete conversion if the reaction is conducted at the feed side of the Pt-Pd/SiO$_2$/V membrane described in Example 9 such that hydrogen is removed from the feed side of the membrane. If the partial pressure of hydrogen at the feed side of the membrane is sufficiently low, then H$_2$S decomposition can be driven to essentially 100% conversion. An important process-design parameter is the residence time required to achieve complete conversion. Shorter residence times will lead to smaller membrane reactors and, thus, to a reduction in costs.

Figure 15:
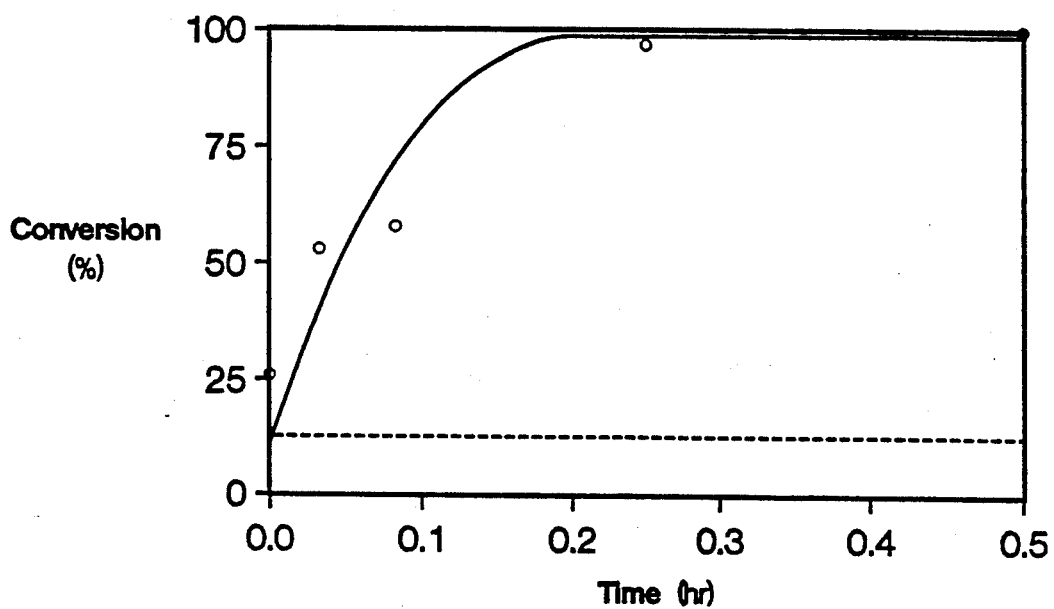

Conversion was evaluated as a function of residence time at 700° C. for a feed stream containing 1.5% H$_2$S in the graph comprising FIG. 15. This graph illustrates three important points.

First, the membrane reactor is effective at driving the decomposition of H$_2$S essentially to completion—the experimentally measured conversion was greater than 99.3%. In comparison, without hydrogen removal from the feed side of the membrane, the equilibrium conversion was only 13% under the experimental conditions, indicated by the dashed horizontal line.

Second, the experimental data indicated that the rate of the H$_2$S decomposition reaction is very fast relative to the rate at which hydrogen is transported across the metal membrane. Thus, even at residence times on the order of 1 second, the H$_2$S decomposition has already reached the 13% equilibrium conversion. For the reaction to proceed beyond this value hydrogen must permeate the membrane. Accordingly, the plot of conversion against residence time can be divided into two regimes. First is the regime between 0% and 13% conversion, dominated by the reaction kinetics for H$_2$S decomposition (hydrogen flux is not significant). The second regime is between 13% and 100% conversion, in which the hydrogen flux is rate-limiting. Since the hydrogen flux is slow relative to the chemical reaction kinetics, the slope of the curve is less steep in the second regime (flux-dominated) than in the first regime (reaction kinetics-dominated).

Finally, the experimental data are accurately described by a simple mathematical model as shown by the solid line in FIG. 15. This model assumes that the chemical rate for H$_2$S decomposition is very fast relative to the rate at which hydrogen is transported across the metal membrane. Under these conditions the feed gas is always at equilibrium at the feed side of the membrane, and the composition of the feed can be calculated if the hydrogen partial pressure is known. The membrane flux, then, defines the composition of the feed gas and the time required to achieve 100% conversion. In other words, the system can be modeled as if it consisted of a pure hydrogen feed at a partial pressure defined by the equilibrium constant for H$_2$S thermal decomposition.

Figure 16:
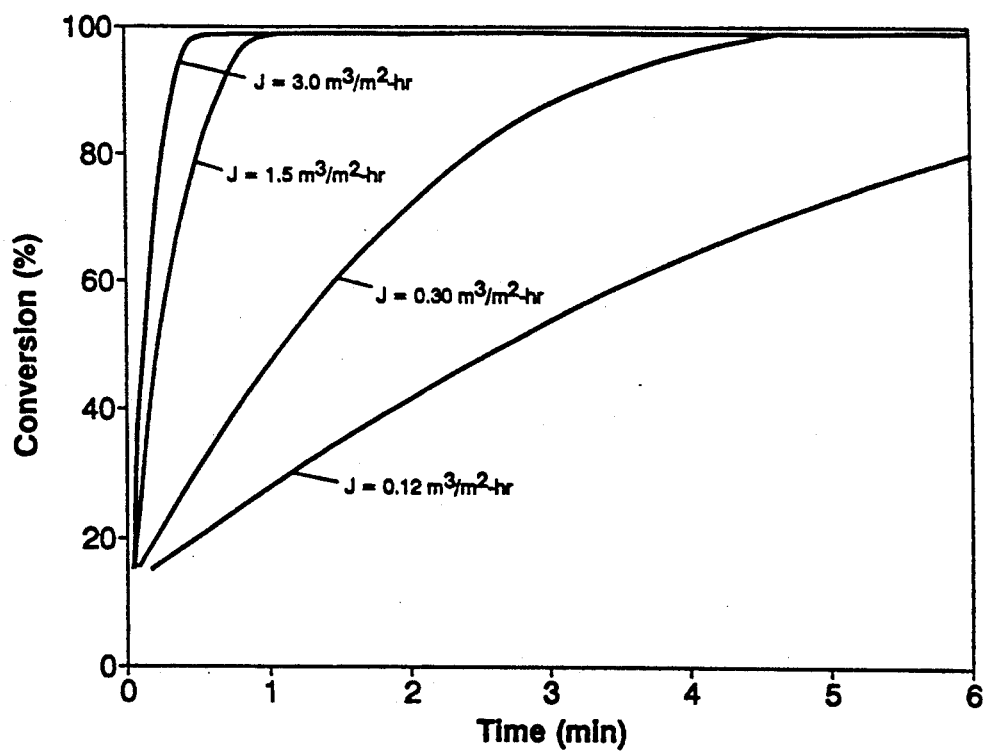

Using this model, the rate of H$_2$S conversion at the feed surface of a Pt-Pd/SiO$_2$/V membrane was calculated for membranes with higher hydrogen flux than the membrane described above in this Example. Pt-Pd/SiO$_2$/V membranes with higher flux will result from decreasing the 25-$\mu$m thickness of the platinum layer. The results of this modeling study are presented in FIG. 16 and suggest that reasonably short residence times (about 30 seconds) can be achieved by increases in the hydrogen flux.

EXAMPLE 13

A unique aspect of the Pt-Pd/SiO$_2$/V composite-metal membrane described in Example 9 is that the membrane does not degrade during exposure to H$_2$S. This chemical resistance to H$_2$S is due to the Pt coating of the composite metal membrane. Metal membranes coated by other materials (e.g., palladium, nickel, iron, and their alloys) rapidly undergo irreversible chemical reaction with H$_2$S, resulting in a dramatic decrease in membrane permeability and/or physical destruction of the membrane. During tests lasting up to 8 hrs, the Pt-coated composite metal membrane showed no change in flux using a pure H$_2$S feed at 115 psia and at 700° C.

For comparison, a Pd/SiO$_2$/V composite metal membrane, nominally identical to the Pt-Pd/SiO$_2$/V metal membrane except for the feed-side coating layer, was also subjected to 115 psia H$_2$S (also at 700° C.). The Pd-coated metal membrane failed by catastrophic rupture within seconds. The membrane was subsequently found to have suffered from severe corrosion by H$_2$S of the Pd coating and the vanadium base metal, resulting in numerous perforations of the membrane.

The terms and expressions which have been employed in the foregoing specification are used therein as terms of description and not of limitation, and there is no intention in the use of such terms and expressions of excluding equivalents of the features shown and described or portions thereof, it being recognized that the

What is claimed is:

1. A method for separating hydrogen from other gases comprising:
   (a) providing a gaseous feed stream containing hydrogen, said feed stream being selected from coal-derived and petroleum-derived gas;
   (b) contacting said feed stream at a temperature of at least 700° C. and a pressure of at least 100 psia with a composite metal membrane; and
   (c) separating hydrogen that permeates through said membrane wherein said membrane comprises a hydrogen-permeable base metal and a hydrogen-permeable coating metal that are separated by a barrier which prevents intermetallic diffusion between said base metal and said coating metal at a temperature of at least 700° C., and the partial pressure of hydrogen on the permeate side of said membrane is less than the partial pressure of hydrogen on the feed side of said membrane.

2. A method for the thermal decomposition of hydrogen sulfide comprising:
   (a) providing a gaseous feed stream comprising at least one hydrogen sulfide-containing gas;
   (b) contacting said gaseous feed stream at a temperature of at least 700° C. and a pressure of at least $10^{-4}$ psia with a composite metal membrane; and
   (c) separating hydrogen that permeates through said membrane wherein said membrane comprises a hydrogen-permeable base metal and a hydrogen-permeable coating metal that is resistant to chemical attack by hydrogen sulfide, said base metal and coating metal being separated by a barrier which prevents intermetallic diffusion between said base metal and said coating metal at a temperature of at least 700° C., and the partial pressure of hydrogen on the permeate side of said membrane is less than the partial pressure of hydrogen on the feed side of said membrane.

3. The method of claim 1 or 2 wherein said barrier of said membrane comprises an inorganic proton conductor other than pure metal or a pure metal alloy.

4. The method of claim 1 or 2 wherein said barrier of said membrane is selected from the group consisting essentially of oxides of molybdenum, silicon, tungsten and vanadium, and sulfides of molybdenum, tungsten and vanadium.

5. The method of claim 1 or 2 wherein said base metal of said membrane is selected from hydrogen-permeable transition metals from Groups IIIB, IVB, VB VIIB and VIIIB of the periodic table and alloys containing $\geq 20\%$ of said metals.

6. The method of claim 5 wherein said coating metal is platinum.

7. The method of claim 1 or 2 wherein a sweep gas is used on the permeate side of said membrane.

8. The method of claim 7 wherein said sweep gas is noncondensable.

9. The method of claim 8 wherein said noncondensable sweep gas is air.

10. The method of claim 7 wherein said sweep gas is condensable.

11. The method of claim 10 wherein said condensable sweep gas is water vapor.

12. The method of claim 11 wherein said water vapor is condensed and revaporized and recycled as said sweep gas.

13. The method of claim 2 wherein a vacuum pump is used on the permeate side of said membrane.

14. The method of claim 1 wherein the raffinate from said gaseous feed stream is contacted with a second of said membrane and air is used as a sweep gas on the permeate side of said second membrane.

15. The method of claim 1 wherein the partial pressure of hydrogen in said gaseous feed stream is at least 50 psia, the partial pressure of hydrogen that permeates through said membrane is at least 25 psia, the raffinate from said gaseous feed stream is contacted with a second of said membrane, a condensable gas is used as a sweep gas on the permeate side of said second membrane, said sweep gas is condensed to liberate hydrogen therefrom, and said condensed sweep gas is vaporized and recycled as sweep gas.

* * * * *

UNITED STATES PATENT AND TRADEMARK OFFICE
CERTIFICATE OF CORRECTION

PATENT NO. : 5,217,506
DATED : June 8, 1993
INVENTOR(S) : David J. Edlund and Dwayne T. Friesen It is certified that error appears in the above-indentified patent and that said Letters Patent is hereby corrected as shown below:

Col. 1, line 6: insert -- , DE-FG03-92ER81419 -- after "91ER81228"

Col. 3, line 45: delete the dash (-) between "A" and "B" and insert an arrow (→)

Col. 4, line 17: delete the dash (-) between "$H_2O$" and "$CO_2$" and insert an arrow (→)

Col. 4, line 54: delete "conversation" and insert -- conversion --

Col. 11, line 14: delete "influx" and insert flux --

Col. 12, line 10: delete "he" and insert -- the --

Col. 12, line 26: delete "temperate" and insert -- temperature --

Signed and Sealed this

Thirtieth Day of August, 1994

Attest:

BRUCE LEHMAN

Attesting Officer       Commissioner of Patents and Trademarks